United States Patent [19]

McAfee et al.

[11] Patent Number: 5,525,564

[45] Date of Patent: Jun. 11, 1996

[54] PLATINUM CATALYST AND A CURABLE ORGANOPOLYSILOXANE COMPOSITION CONTAINING SAID PLATINUM CATALYST

[75] Inventors: Richard McAfee; James R. Adkins; John C. Getson, all of Adrian, Mich.

[73] Assignee: Wacker Silicones Corp., Adrian, Mich.

[21] Appl. No.: 224,372

[22] Filed: Apr. 7, 1994

Related U.S. Application Data

[62] Division of Ser. No. 58,339, May 6, 1993, Pat. No. 5,328,974.

[51] Int. Cl.[6] ................................................ C08G 77/06
[52] U.S. Cl. ................................................ 502/150; 502/169
[58] Field of Search ................................ 502/150, 169

[56] References Cited

FOREIGN PATENT DOCUMENTS

| | | |
|---|---|---|
| 57459 | 8/1982 | European Pat. Off. . |
| 173512 | 3/1986 | European Pat. Off. . |
| 219720 | 4/1987 | European Pat. Off. . |
| 416471 | 3/1991 | European Pat. Off. . |
| 491509 | 6/1992 | European Pat. Off. . |

OTHER PUBLICATIONS

Cotton and Wilkinson, Advanced Inorganic Chemistry, Third Edition (1972), Interscience, p. 998.

Gmelins Handbuch Der Anorganischen Chemie, 8th edition, Platin, Teil D, Verlag Chemie GmbH, 1957, pp. 409 and 440.

*Primary Examiner*—Asok Pal
*Attorney, Agent, or Firm*—Martin Connaughton

[57] ABSTRACT

A platinum catalyst which is prepared by reacting a platinum halide with an organic compound having at least one —C≡C— group in the presence or absence of a base to form a complex which promotes the addition of silicon-bonded hydrogen atoms to silicon-bonded aliphatic unsaturated hydrocarbon groups in the presence of no-clean flux.

6 Claims, No Drawings

PLATINUM CATALYST AND A CURABLE ORGANOPOLYSILOXANE COMPOSITION CONTAINING SAID PLATINUM CATALYST

This application is a division of application Ser. No. 08/058,339, filed May 6, 1993, now U.S. Pat. No. 5,328,974.

The present invention relates to a platinum catalyst and more particularly a curable organopolysiloxane composition containing a platinum catalyst which is not inhibited by no-clean flux.

BACKGROUND OF THE INVENTION

When electrical components are connected together, for example, to form a circuit board, the electrical components are very susceptible to various contaminants such as dirt and moisture, particularly if they are stored for a considerable period of time. Additionally, the components are subject to various contaminants and moisture and may be damaged when they are attached to a substrate such as a circuit board. To avoid this problem, coatings have been applied to cover the components or circuit board containing the electrical components.

The electrical components and/or circuit boards have been coated with organopolysiloxane compositions to protect the components from moisture, contamination and damage. However, it has been found that organopolysiloxane compositions which cure by the addition of silicon bonded hydrogen atoms to organopolysiloxanes having olefinic unsaturation in the presence of a platinum catalyst do not cure at the interface of the metallic connectors. It is believed that the no-clean flux, i.e., flux which is not removed after soldering electrical components, inhibits curing of these organopolysiloxane compositions.

Therefore, this invention relates to a platinum catalyst and a one-component organopolysiloxane composition containing a hydrosilation catalyst which may be applied to circuit boards and/or hybrid circuitry to form a curable coating thereon.

Organopolysiloxanes which are curable by the reaction of silicon-bonded, terminally unsaturated olefinic radicals and silicon bonded hydrogen atoms in the presence of hydrosilation catalysts such as platinum compounds and complexes thereof are well known and are disclosed, for example, in U.S. Pat. No. 3,419,593 to Willing and U.S. Pat. No. 4,450,283 to McAfee et al.

Platinum catalysts which have been employed to promote the hydrosilation reactions such as the addition of organosilicon compounds containing $\equiv$SiH groups to organosilicon compounds containing aliphatic unsaturation are complexes such as described in U.S. Pat. No. 3,775,452 to Karstedt, in which an unsaturated organosilicon compound is reacted with a platinum halide and thereafter treating the resultant mixture with a base to remove the available inorganic halogen.

Another platinum complex which may be used in the hydrosilation reactions is described in U.S. Pat. No. 4,603,215 to Chandra et al., in which the platinum complex is prepared by reacting a platinum vinylsiloxane complex prepared in accordance with U.S. '593 to Willing and U.S. '452 to Karstedt. In general these platinum-vinylsiloxane complexes are prepared by contacting a vinylsiloxane such as described above with a platinum compound such as chloroplatinic acid ($H_2PtCl_6 \cdot 6H_2O$). The resultant platinum-vinylsiloxane complex is then contacted with an alkyne to form a platinum alkyne complex. Also, U.S. Pat. No. 3,445,420 to Kookootsedes et al., discloses an organopolysiloxane composition comprising a mixture of an olefin containing organosilicon polymer, an organosilicon compound containing silicon-bonded hydrogen atoms, a platinum catalyst and an acetylenic compound as an inhibitor.

One of the disadvantages of the organopolysiloxanes described above is that they must be mixed just prior to use. When inhibitors are incorporated in these compositions and they are stored for a period of time before use, they will not cure or will cure very slowly in the presence of no-clean flux.

Therefore, it is an object of the present invention to provide a one-component organopolysiloxane composition which cures in the presence of no-clean flux. Another object of the present invention is to provide a circuit board having a cured coating thereon. Still another object of the present invention is to provide a platinum catalyst which promotes curing of an organopolysiloxane composition in the presence of no-clean flux. A further object of the present invention is to provide a process for preparing a platinum catalyst which promotes the addition of $\equiv$SiH groups to Si-bonded aliphatic unsaturated hydrocarbon groups. A still further object of the present invention is to provide a platinum catalyst which is not inhibited by no-clean flux.

SUMMARY OF THE INVENTION

The foregoing objects and others which will become apparent from the following description are accomplished in accordance with this invention, generally speaking, by providing a platinum catalyst which promotes the addition of silicon-bonded hydrogen atoms to silicon-bonded aliphatic unsaturated hydrocarbon groups in the presence of no-clean flux. The platinum catalyst is prepared by reacting a platinum halide with an organic compound having at least one —C$\equiv$C— group in the presence or absence of a base to form a complex.

DESCRIPTION OF THE INVENTION

The synthesis of platinum complexes are described in, for example, F. Gordon A. Stone, Ligand-Free Platinum Compounds, Acc. Chem. Res. 1981, 14, 317–327, where platinum complexes are prepared using platinum bis(cyclooctadiene) complexes.

N. Boag et al., J. C. S. Dalton (1980) pg. 2170 et seq. describe a number of platinum complexes synthesized via platinum bis(cyclooctadiene) complexes and platinum tris-(ethylene) complexes.

The platinum catalyst of this invention is preferably prepared by reacting a platinum halide with an organic compound having at least one —C$\equiv$C— group at an elevated temperature in the presence of sufficient base to remove the available inorganic halogen.

Platinum halides which can be employed in this invention are, for example, $H_2PtCl_2 \cdot nH_2O$ and metal salts such as $NaHPtCl_6 \cdot nH_2O$, $KHPtCl_6 \cdot nH_2O$, $NaPtCl_6 \cdot nH_2O$, $K_2PtCl_6 \cdot H_2O$.

Examples of organic compounds having at least one —C$\equiv$C— group per molecule are those of the formula R—C$\equiv$C—R', where R and R' which may be the same or different represent hydrogen, or a monovalent hydrocarbon radical having from 1 to 18 carbon atoms or a monovalent hydrocarbon radical having from 1 to 18 carbon atoms which is substituted with a radical of the formula —C$\equiv$C—, a hydroxyl group, an oxygen atom, a carboxyl

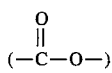

radical, a carbonyl

radical and a silyl or siloxy group.

Examples of radicals represented by R and R' include alkyl radicals such as the methyl, ethyl, n-propyl, isopropyl, dodecyl and octadecyl radicals; cycloalkyl radicals such as the cyclobutyl, cyclopentyl, cyclohexyl and cyclodecyl radicals; aryl radicals such as the phenyl, xenyl, naphthyl and the phenanthryl radicals; aralkyl radicals such as the benzyl, B-phenylethyl and B-phenylpropyl radicals and alkaryl radicals such as the tolyl, xylyl and ethylphenyl radicals.

Specific examples of organic radicals represented by R and R' are —C(CH$_3$)$_2$(OH), —C(CH$_3$)(C$_2$H$_5$), —C(C$_2$H$_5$)$_2$(OH), —C(CH$_3$)(C$_3$H$_7$)(OH), —C(C$_5$H$_{11}$)(CH$_3$)(OH), —C(C$_2$H$_5$)(C$_3$H$_7$)(OH), —C(CH$_3$)$_3$, —C(C$_6$H$_4$CH$_3$), —Si(CH$_3$)$_3$,

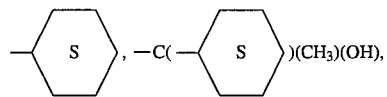

—Si(CH$_3$)$_2$)OSi(CH$_3$)$_3$, and —Si(CH$_3$)$_2$(CH$_2$)$_2$—Si(CH$_3$)$_3$.

Specific examples of organic compounds having at least one —C≡C— group of the formula are

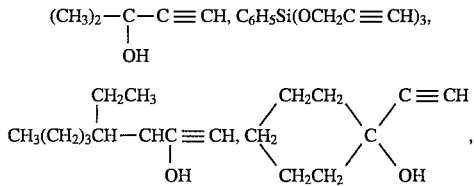

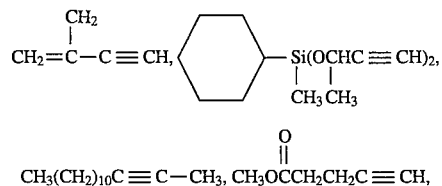

CH$_3$(CH$_2$)$_{10}$C≡C—CH$_3$, CH$_3$OCCH$_2$CH$_2$C≡CH,

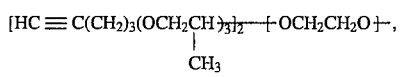

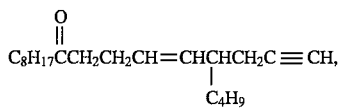

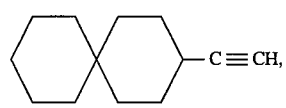

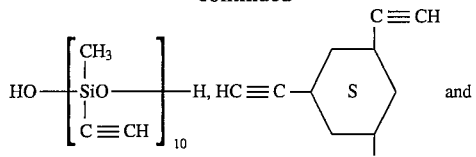

HC≡C(CH$_2$)$_{10}$CH(CH$_2$)$_4$C≡CH.
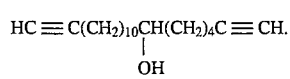

Other organic compounds which may be employed having at least one —C≡C— group are butyne-2, phenylacetylene, 2-ethynylisopropanol, 2-ethynylbutane 2-ol, 1 hexyne 3-ol, 2,5 dimethyl-3-hexyne-2,5-diol, 3,6-dimethyl-4-octyne-3,6-diol, 2,4,7,9-tetramethyl-5-decyne-4,7-diol, 3,5-dimethyl-1-hexyne-3-ol and ethynylcyclohexanol. The preferred organic compounds are butyne-2, 2-ethynylisopropanol, 2-ethynylbutane-2-ol and ethynylcyclohexanol.

Preferably the monovalent hydrocarbon radicals and substituted monovalent hydrocarbon radicals represented by R and R' are free of olefinic unsaturation, such as vinyl and allyl radicals.

The platinum catalysts of this invention are prepared by reacting a platinum halide with an organic compound having at least one —C≡C— group per molecule in the presence or absence of a base and optionally in the presence of a suitable solvent at an elevated temperature. The platinum halide and organic compound may be reacted in the absence of the base and thereafter the resultant platinum complex may be reacted with the basic material to substantially reduce the halogen content of the resultant platinum catalyst.

The reaction of the platinum halide and organic compound having at least one —C≡C— group may be conducted at a temperature of from about 20° up to about 125° C. and more preferably from 40° to 75° C.

The reaction of the platinum halide with the organic compound is preferably conducted at atmospheric pressure; however, it may be conducted at pressures below and above atmospheric pressure.

Bases which may be employed in preparing the platinum catalysts of this invention are, for example, alkali metal carbonates such as sodium carbonate, potassium carbonate, sodium bicarbonate; alkaline earth metal carbonates and bicarbonates and alkali hydroxides such as sodium hydroxide and potassium hydroxide.

The amount of base employed is not critical; however, an amount in excess of that required to neutralize all available inorganic halogen to form the corresponding salts provides for effective results. Less than the stoichiometric amount can be employed, but at least that amount must be employed to provide for the removal of available inorganic halogen.

It is preferred that sufficient organic compound be employed so that at least one —C≡C— group is present for every atom of platinum, and more preferably a two-fold or more molar excess of organic compound having at least one —C≡C— group is highly desirable. Such a molar excess assures that all of the platinum present is complexed with the organic compound.

Solvents may be employed in the preparation of the platinum catalysts of this invention. Examples of suitable solvents are alcohols having from 1 to 6 carbon atoms such as methanol, ethanol, propanol, butanol and hexanol and aromatic hydrocarbon solvents such as benzene toluene and xylene. Preferably the solvent employed is an alcohol and more preferably ethanol. Mixtures of alcohols or alcohols and aromatic hydrocarbons may be used. The nature of the solvent can vary depending on the type of platinum halide employed as well as the nature of the organic compound having at least one —C≡C— group per molecule.

When undesirable materials, such as salts are associated with the platinum catalysts of this invention, the solvent can be stripped from the reaction mixture and then the platinum catalyst can be extracted with a suitable solvent such as a non-polar hydrocarbon solvent, followed by filtration.

Other solvents which may be employed are unsaturated siloxanes. Examples of unsaturated siloxanes which may be employed are sym-divinyltetramethyldisiloxane, 1,1-divinyltetramethyldisiloxane, hexavinyldisiloxane, sym-divinyltetraphenyldisiloxane, 1,1,3-trivinyltrimethyldisiloxane, and sym-tetravinyldimethyldisiloxane and cyclosiloxanes such as 1,3,5-trivinyl-1,3,5-trimethylcyclotrisiloxane, 1,3,5, 7-tetraallyl-1,3,5,7-tetraphenylcyclotetrasiloxane and 1,3-divinyloctamethylcyclopentasiloxane. When a disiloxane is employed having olefinic unsaturation, it is preferably added after the platinum halide is reacted with the organic compound having at least one —C≡C— group per molecule in the presence of a base.

The amount of solvent is not critical and may range from about 1 to 100 parts and more preferably from 10 to 50 parts of solvent per part of platinum halide and organic compound having at least one —C≡C— group per molecule.

The platinum catalysts of this invention are effective for the addition of organopolysiloxanes containing aliphatically unsaturated groups to organohydrogenpolysiloxanes to form elastomers. The platinum catalysts of this invention are effective for the addition reactions described in U.S. Pat. No. 2,823,218 to Speier et al., U.S. Pat. No. 2,970,150 to Bailey and U.S. Pat. No. 3,220,972 to Lamoreaux.

The platinum catalysts of this invention are employed, in a heat curable organopolysiloxane composition containing (a) an organopolysiloxane having an average of at least two aliphatically unsaturated monovalent hydrocarbon radicals per molecule, (b) an organohydrogenpolysiloxane having an average of at least two silicon-bonded hydrogen atoms per molecule, (c) the platinum catalyst, and (d) optionally, fillers.

The organopolysiloxanes having aliphatic unsaturation generally have recurring units of the formula

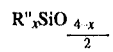

where R" is selected from the group consisting of monovalent hydrocarbon radicals and halogenated monovalent hydrocarbon radicals in which an average of at least two of the monovalent hydrocarbon radicals contain aliphatically unsaturated groups per molecule and x is an integer of from 1 to 3, with an average value of from about 1.7 to about 2.1.

It is preferred that the hydrocarbon radicals and substituted hydrocarbon radicals represented by R" each contain from 1 to 18 carbon atoms. Examples of suitable hydrocarbon radicals are alkyl radicals, such as the methyl, ethyl, n-propyl and isopropyl radicals, as well as the octadecyl radicals; cycloalkyl radicals such as the cyclohexyl and the cycloheptyl radicals; aryl radicals such as the phenyl radical; alkaryl radicals such as the tolyl radical and aralkyl radicals such as the benzyl and the beta-phenylethyl radicals. Examples of substituted hydrocarbon radicals represented by R are halogenated hydrocarbon radicals, such as the 3,3,3-trifluoropropyl radical and o-, m- and p-chlorophenyl radicals. Because of their availability, it is preferred that at least 80% of the R" radicals be methyl radicals.

Examples of hydrocarbon radicals R" having aliphatic unsaturation are vinyl, allyl, methallyl and butadienyl radicals, with vinyl being the preferred radical.

These organopolysiloxanes preferably have a viscosity of from about 5 to 10,000,000 mPa·s at 25° C. and more preferably from about 40 to about 500,000 mPa·s at 25° C.

The organopolysiloxanes employed in the compositions of this invention are produced by the hydrolysis and condensation of the corresponding hydrolyzable silanes. These organopolysiloxanes are preferably linear polymers containing diorganosiloxane units of the formula R"$_2$SiO; however, these polymers may also contain minor amounts of other units, such as R"SiO$_{3/2}$ units, R"$_3$SiO$_{0.5}$ and/or SiO$_{4/2}$ units, in which R" is the same as above.

The preferred organopolysiloxane is a diorganopolysiloxane having the general formula

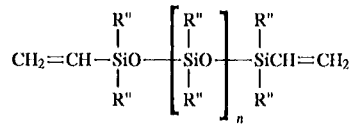

where n is a number such that the organopolysiloxane has a viscosity of from about 40 to 100,000 mPa·s at 25° C.

The organohydrogenpolysiloxanes employed in the compositions of this invention generally consist of units of the general formula

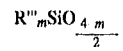

where R'" represents a hydrogen atom or R", where R" represents a monovalent hydrocarbon radical or a halogenated monovalent hydrocarbon radical having from 1 to 18 carbon atoms, in which at least two and preferably three Si-bonded hydrogen atoms are present per molecule and m is an integer of from 1 to 3, with an average of from 1.7-to 2.2. Preferred compounds are those consisting of R'"SiO— units, R'"$_2$SiO— and R'"$_3$SiO$_{0.5}$— units, in which an Si-bonded hydrogen atom is present for each 3 to 100 silicon atoms and R'" is the same as above. It is preferred that the organohydrogenpolysiloxanes have a viscosity of from about 10 to 50,000 mPa.s and more preferably from 100 to 20,000 mPa.s at 25° C.

The organohydrogenpolysiloxanes may also contain monovalent hydrocarbon radicals having aliphatic unsaturation as well as Si-bonded hydrogen atoms in the same molecule.

It is preferred that the organohydrogenpolysiloxanes contain from 0.002 to about 1.7% by weight of Si-bonded hydrogen atoms, and the silicon valences not satisfied by hydrogen atoms or siloxane oxygen atoms are satisfied by unsubstituted or substituted monovalent hydrocarbon radicals free of aliphatic unsaturation.

The organohydrogenpolysiloxanes having an average of at least 2 Si-bonded hydrogen atoms per molecule are preferably present in the compositions of this invention in an amount of from about 0.1 to about 15 Si-bonded hydrogen atoms per aliphatically unsaturated group.

The platinum catalyst is generally employed in an amount of from about 0.5 to 300 ppm by weight and more preferably from about 2 to 50 parts per million (ppm) by weight calculated as platinum and based on the weight of the organopolysiloxane (a) and organohydrogenpolysiloxane (b).

Fillers which may be incorporated in the compositions of this invention are reinforcing fillers, i.e., fillers having a surface area of at least 50 m²/gm. Examples of such fillers are precipitated silicon dioxide having a surface area of at least 50 m²/gm and/or pyrogenically produced silicon dioxide. Examples of other reinforcing fillers are the aerogels, alumina, carbon blacks and graphite.

A portion of the fillers can be semi- or non-reinforcing fillers, i.e., fillers which have a surface area of less than 50 $m^2/gm$. Examples of semi- or non-reinforcing fillers are metal oxides, metal nitrides, cork, organic resins, polytetrafluoroethylene, polychlorotrifluoroethylene, polyvinyl chloride, carbon black, graphite, bentonite, diatomaceous earth, crushed quartz, mica, metal fibers, glass beads, bubbles or fibers and mixtures thereof. Preferred examples of metal oxides are zinc oxide, ferric oxide, alumina and titanium oxide. The fillers may also be treated with, for example, triorganoalkoxysilanes, such as trimethylethoxysilane to coat the surfaces with organosiloxy groups.

The amount of fillers which may be incorporated in the compositions of this invention is not critical and may vary over a wide range. Thus, the amount of filler may range from about 1 to 80% by weight, preferably from about 5 to 75% by weight, and more preferably from about 10 to 50% by weight, based on the weight of the composition, i.e., the weight of the organopolysiloxane, the organohydrogenpolysiloxane, the platinum catalyst and the filler.

Other additives which may be incorporated in the compositions of this invention include pigments, compression set additives, oxidation inhibitors, plasticizers, adhesion promoters, base stabilizers, compounds which inhibit curing, and other materials commonly employed as additives in the silicone rubber art. Such additives are preferably present in an amount below about 15% by weight based on the weight of the composition.

Compounds which may be employed in the compositions of this invention to inhibit platinum catalyzed addition reactions are benzotriazole, acetylenic compounds such as acetylenically unsaturated secondary or tertiary alcohols, tetramethylquanidine acetate, ethylenically unsaturated isocyanurate, phenylhydrazine, a diaziridine, dithiocarbamic acid, thiuram monosulfides, 2 mercaptobenzothiazole, hydrazone and the like.

The compositions of this invention are mixed in any desired order. For example, the organopolysiloxane containing aliphatic unsaturation may be mixed with the organohydrogenpolysiloxane in the desired proportions and the desired amount of catalyst then added. A preferred method of mixing is to premix the organopolysiloxane having aliphatic unsaturation with the platinum catalyst and then combine the resultant mixture with the organohydrogenpolysiloxane and optionally, fillers.

The compositions of this invention may be prepared by mixing the components in conventional mixers, such as plantary mixers.

In another embodiment, the platinum catalyst is mixed with the organopolysiloxane having aliphatic unsaturation and then mixed with the organohydrogenpolysiloxane, or it may be combined with the mixture containing the organopolysiloxane having aliphatic unsaturation and the organohydrogenpolysiloxane.

The relative amounts of the Si-bonded hydrogen containing compound and the compound containing aliphatic unsaturation can vary within extremely wide limits. Theoretically, one Si-bonded hydrogen atom is equivalent to one olefinic double bond. For many purposes, however, it may be desirable to employ an excess of one of the reactants to facilitate the completion of the reaction or to insure that the reaction product still contains either unreacted Si-bonded hydrogen atoms or aliphatically unsaturated groups.

The organopolysiloxane composition of this invention is stable; that is, it inhibits curing at room temperature. Generally, these compositions are heated to temperatures in the range of from about 50° to 300° C. and more preferably to a temperature of from 100° to 175° C. for curing. The cure time depends on such things as the reactants employed and the amount and type of catalyst employed.

In some cases, it is desirable to employ a diluent for the catalyst and/or one or both reactants. The diluent should be inert to the reactants and catalyst under the reaction conditions. Examples of suitable diluents are organopolysiloxanes such as trimethylsiloxy-terminated dimethylpolysiloxanes and organic solvents which vaporize at low temperatures. Examples of suitable organic solvents are chlorinated hydrocarbons such as trichloroethylene. When organic solvents are employed, they are preferably employed in an amount of less than 20% by weight based on the weight of the organopolysiloxane composition.

The compositions of this invention can be used for any application where heat curing is possible. These compositions are especially useful as coating compositions and as encapsulating materials for electronic devices. The compositions are especially useful for coating or encapsulating semi-conductors where no-clean flux is present because the flux does not substantially inhibit curing of the organopolysiloxane composition. This is especially important where these semi-conductors are coated on an assembly line. In addition these compositions may be used as adhesive repellent coatings and as fabric coatings. Also, these compositions are especially useful in injection molding processes.

The heat curable organopolysiloxane compositions of this invention have excellent storage stability at room temperature. In addition, the curing system of this invention can serve to control the rate of curing of a platinum catalyzed curing system. In the following examples all parts and percentages are by weight unless otherwise specified.

Preparation of platinum complex

EXAMPLE 1

A platinum complex is prepared by adding 2.9 parts of sodium bicarbonate and 22.6 parts of ethynylcyclohexanol to a flask and thereafter heating the mixture to about 45° C. To the flask is added a mixture containing 1.2 parts of chloroplatinic acid ($H_2PtCl_6.6H_2O$) dissolved in 15 parts of ethanol. The reaction mixture is heated for about 2 hours at about 50° C. with the evolution of gas and then filtered at room temperature. The resultant material is vacuum stripped in a roto-evaporator at room temperature for 8 hours. About 12.1 parts of a reddish black liquid product is recovered containing about 3700 ppm of elemental platinum.

EXAMPLE 2

A platinum complex is prepared by mixing 50 parts of ethynylcyclohexanol with a solution containing 46 parts of ethanol and 9.3 parts of chloroplatinic acid ($H_2PtCl_6.6H_2O$) in a flask. Then 15 parts of sodium bicarbonate are added the flask and the contents heated to about 55° C. and maintained at this temperature for a period of about 4 hours. The resultant material is cooled to room temperature, then filtered and the residue washed with isopropanol. The resultant solution was vacuum stripped in a roto-evaporator for 6 hours at room temperature. The material was placed in a dessicator and vacuum stripped for 12 additional hours,

EXAMPLE 3

A platinum complex is prepared by adding 2,9 parts of sodium bicarbonate and 22.6 parts of ethynylcyclohexanol to a flask and thereafter heating the contents to about 45° C. About 1.2 parts of chloroplatinic acid ($H_2PtCl_6.6H_2O$) dissolved in 15 parts of ethanol are added to the flask. The reaction mixture is heated for about 2 hours at about 50° C. with the evolution of gas and then filtered at room temperature. The resultant material is vacuum stripped in a rotoevaporator at room temperature for about 8 hours. About 12.1 parts of a reddish black liquid is recovered containing about 3700 ppm of elemental platinum. The resultant reddish black liquid is then mixed with 12.1 parts of a vinylmethyldisiloxane $(ViMe_2Si)_2O$.

EXAMPLE 4

The procedure of Example 1 is repeated except that 16 parts of 2 methyl-3-butyn-2-ol are substituted for 22.6 parts of ethynylcyclohexanol.

Preparation of a curable silicone composition

EXAMPLE 5

About 750 parts of vinyl-terminated dimethylpolysiloxane having a viscosity of 500 mPa·s at 25° C. is mixed with 4 parts of the platinum complex prepared in accordance with the procedure described in Example 1. About 0.75 part of ethynylcyclohexanol is added to the mixture with mixing and then 22.5 parts of a methylhydrogenpolysiloxane are added to the mixture. The resultant mixture is mixed for about 30 minutes, then applied to an alumina substrate coated with no-clean flux and cured at 110° C. for 10 minutes. The resultant composition cured at the interface between the flux and the organopolysiloxane composition to form an elastomer which showed good adhesion to the flux.

EXAMPLE 6

The procedure of Example 5 is repeated except that 6 parts of the platinum complex prepared in Example 2 is substituted for the platinum complex of Example 1. When the resultant composition is applied to an alumina substrate coated with no-clean flux and cured at 110° C. for 10 minutes, the resultant composition cured at the interface between the flux and the organopolysiloxane composition to form an elastomer which exhibited good adhesion to the flux.

EXAMPLE 7

The procedure of Example 5 is repeated except that 8 parts of the platinum complex prepared in Example 3 is substituted for the 4 parts of the platinum complex prepared in accordance with Example 1. When the resultant composition is applied to an alumina substrate coated with no-clean flux and cured at 110° C. for 10 minutes, the elastomer cured at the interface between the flux and the silicone elastomer.

COMPARISON EXAMPLE $V_1$

The procedure of Example 5 is repeated except that a platinum complex prepared in accordance with Example 1 of U.S. Pat. No. 3,775,452 to Karstedt containing 20 ppm of elemental platinum is substituted for the platinum complex of Example 1. When the resultant composition is applied to an alumina substrate coated with no-clean flux and cured at 110° C. for 10 minutes, the resultant elastomer exhibited poor adhesion to the flux and is easily removed from the substrate. The elastomer at the interface with the flux is uncured.

COMPARISON EXAMPLE $V_2$

The procedure of Example 5 is repeated except that the platinum complex prepared in accordance with Example 1 of U.S. Pat. No. 3,419,593 to Willing, containing 20 ppm of elemental platinum is substituted for the platinum complex of Example 1. When the resultant composition is applied to an alumina substrate coated with the no-clean flux and cured at 110° C. for 10 minutes, the resultant elastomer exhibited poor adhesion to the flux and is easily removed from the substrate. The elastomer at the interface with the flux is uncured.

What is claimed is:

1. A process for preparing a platinum catalyst which comprises reacting a platinum halide with an organic compound having at least one —C≡C— group represented by the formula

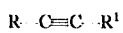

where R and $R^1$ each represent hydrogen or a monovalent hydrocarbon radical, or a monovalent hydrocarbon radical which is substituted with a radical of the formula —C≡C—, a hydroxyl group, an oxygen atom, a carboxyl radical or a carbonyl radical and thereafter recovering a platinum catalyst.

2. The process of claim 1, wherein the reaction is conducted at a temperature of from 20° C. to 125° C.

3. The process of claim 1, wherein the platinum halide and organic compound having at least one —C≡C— group per molecule are reacted in the presence of a base.

4. The process of claim 3, wherein the base is an alkali metal carbonate, an alkali metal bicarbonate, an alkaline earth metal carbonats, an alkaline earth metal bicarbonate or an alkali hydroxide.

5. The process of claim 1, wherein the platinum halide and organic compound having at least one —C≡C— group per molecule are reacted to form a complex and the resultant complex is then reacted with a base.

6. The process of claim 1, wherein the organic compound is present in an amount such that at least one —C≡C— group is present for each platinum atom.

* * * * *